Aug. 4, 1942. J. H. NICOLAS Plant Pat. 537
ROSE
Filed Dec. 18, 1941
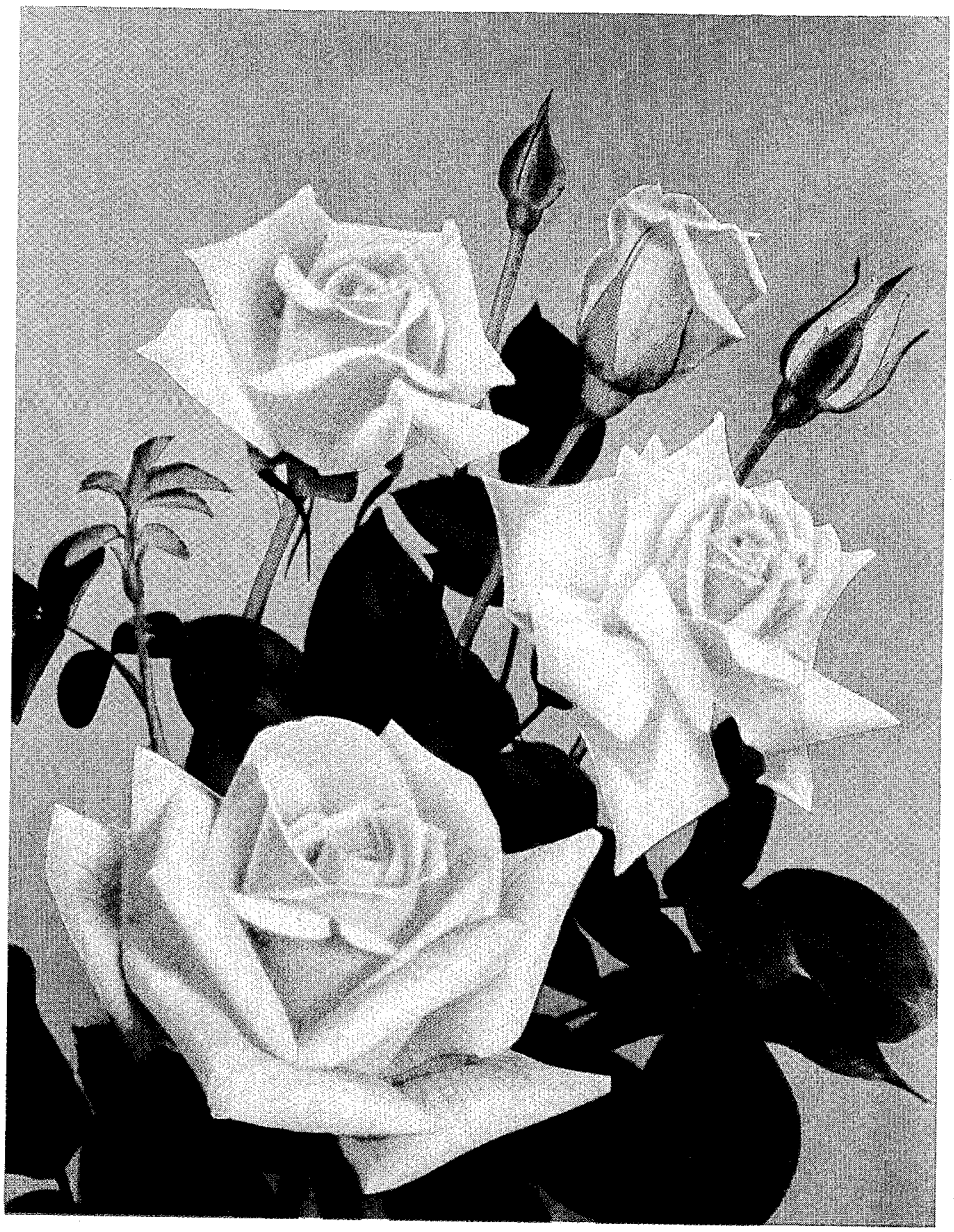
Inventor.
Jean H. Nicolas
By Fannie Nicolas
Administratrix of the Estate
of Jean H. Nicolas, deceased.
By Robbins & Robbins
Attorneys Patented Aug. 4, 1942

Plant Pat. 537

UNITED STATES PATENT OFFICE

537

ROSE

Jean H. Nicolas, deceased, late of Newark, N. Y., by Fannie Nicolas, administratrix, Newark, N. Y., assignor to Jackson & Perkins Company, Newark, N. Y.

Application December 18, 1941, Serial No. 423,558

1 Claim. (Cl. 47—61)

The present invention relates to a new and distinct variety of rose plant of the hybrid tea class, the result of a definite effort to improve upon the parent varieties and others in the same class.

The new variety is distinctive in respect to a number of important characteristics, among which may be mentioned its vigorous, bushy, heavily-foliaged habit of growth, the very lightly serrated edges of its leaflets, the pointed form of bud, and high centered form of the flower in the unusual color combination thereof in the different stages of development of the blooms.

These features are more particularly pointed out in the following detail description of the new variety and accompanying illustration in color, color terminology being in accord with Ridgway's Color Standard.

Parentage: Seedling.
*Seed parent.*—"Sunkist."
*Pollen parent.*—"Olympiad."
Classification: Botanic and commercial—Hybrid tea.

*Flower*

Observations made at Newark, New York, in the morning of September 9, 1941.

Blooming habit: Recurrent—Continuous.
Bud: *Size.*—Medium.
*Form.*—Long. Is not affected by wet or hot weather.
*Color.*—When petals first divide—Old Rose, Plate 13. When petals begin to unfurl—Begonia Rose, Plate 1, with a suffusion of Light Orange Yellow, Plate 3, about half way up from the base of the petal. When half blown: inside of petals—Eosine Pink, Plate 1, with some indication of Rose Pink, Plate 12; reverse of petals—between Deep Rose Pink, Plate 12, and Begonia Rose, Plate 1, with a suffusion of Orange Buff, Plate 3.
*Sepals.*—Branched; Light Cress Green, Plate 31. Curl back when petals begin to unfurl.
*Calyx.*—*Shape*—funnel. *Size*—broad. *Aspect* — smooth. *Color* — outside — Light Cress Green, Plate 31; inside—Light Lumiere Green, Plate 17.
*Peduncle.* — *Length* — Medium. *Aspect* — Prickly. *Color*—Cress Green, Plate 31. *Strength*—Erect; heavy.
*Opening.*—Bud opens well. Is not affected by adverse conditions.

Bloom:
*Size.*—Large. Average size when fully expanded—4½ to 5 inches.
*Borne.*—Several together.
Stems.—Medium length; strong.
*Form.*—When first open, high center. *Permanence*—retains its form to the end.
*Petalage.*—Double (full but open center). Number of petals under normal conditions—45.
*Color.*—Center of flower—Eosine Pink, Plate 1. Outer petals—between Eosine Pink, Plate 1, and Hermosa Pink, Plate 1. Base of petals (aiglet)—Pale Lemon Yellow, Plate 4. Inside of petals—between Eosine Pink, Plate 1, and Rose Pink, Plate 12, in the upper two-thirds of the petal; lower one-third shows a diffusion of Picric Yellow, Plate 4. Reverse of petals—between Eosine Pink, Plate 1, and Thulite Pink, Plate 26. *General tonality from a distance*—between Eosine Pink, Plate 1 and Hermosa Pink, Plate 1.
*Discoloration.*—General tonality at end of first day—Eosine Pink, Plate 1. Second day—between Eosine Pink, Plate 1, and Thulite Pink, Plate 26. Third day—between Eosine Pink, Plate 1, and Thulite Pink, Plate 26.

Petals:
*Texture.*—Leathery. Is not affected by wet or hot weather.
*Appearance.* — Inside — satiny. Outside — shiny.
*Form.*—Oval.
*Arrangement.*—Imbricated (regularly arranged shinglelike). Petaloids in center—few; small.
*Persistence.*—Drop off cleanly.
*Fragrance.*—Moderate; tea (average hybrid tea scent).
*Lasting Quality*—On the plant—long. As cut flower—long.

Genital organs:
*Stamens, anthers.*—Medium size; many; Deep Chrome, Plate 3; arrangement—regular around styles.
*Stamens, filaments (threads).*—Medium length; light cadmium, Plate 4.
*Pollen.*—Apricot Yellow, Plate 4.
*Styles.*—Bunched; even length; medium size; heavy.
*Stigmas.*—Martius Yellow, Plate 4.
*Ovaries.*—Some protruding from calyx.

*Plant*

Form: Bush.

Growth: Very vigorous; upright.

Foliage: Five to seven leaflets.

*Size.*—Medium.

*Quantity.*—Abundant.

*Color.*—New foliage: upper side—Vandyke Red, Plate 13; mid-rib—Light Hellebore Green, Plate 17; under side—Vandyke Red, Plate 13. Old foliage: upper side—Cress Green, Plate 31; under side—Light Cress Green, Plate 31.

*Shape.*—Oval pointed.

*Texture.*—Upper side—leathery. Under side—rough. *Ribs and veins*—ordinary.

*Edge.*—Serrated (saw toothed).

*Serration.*—Single; small.

*Rachis.*—Rainette Green, Plate 31. Under side—prickles.

*Stipules.*—Medium length; slightly bearded.

*Disease resistance.*—Resistant, as indicated by the fact that plants of this variety have been grown in test gardens where they are exposed to the normal ills of such environment and failed to acquire any of the common diseases.

Wood:

*New wood.*—Courge Green, Plate 17, overlaid with Vandyke Red, Plate 13. *Bark*—rough.

*Old wood.*—Cress Green, Plate 31. *Bark*—rough.

Thorns: (Thorns are divided into thorns, prickles, and short needles.)

*Thorns.*—Quantity—on main stalks from base—ordinary. On laterals from stalk—few. *Form*—flat base; medium length; hooked downward. *Color when young*—Acajou Red, Plate 3. *Position*—irregular.

*Prickles.*—Quantity on main stalks and on laterals—none.

*Short Needles.*—Quantity on main stalks and on laterals—nine.

What is claimed is:

A new and distinct variety of rose plant, characterized as to novelty by its vigorous, bushy, heavily-foliaged habit of growth and the form of its leaflets, buds and high centered flowers, combined with the unusual coloring of the blooms in the different stages of development, substantially as shown and described.

FANNIE NICOLAS,

*Administratrix of the Estate of Jean H. Nicolas, Deceased.*